US011396498B2

United States Patent
Asai et al.

(10) Patent No.: US 11,396,498 B2
(45) Date of Patent: *Jul. 26, 2022

(54) METHOD FOR PRODUCING 2,5-BIS(AMINOMETHYL) TETRAHYDROFURAN

(71) Applicant: Mitsubishi Gas Chemical Company, Inc., Tokyo (JP)

(72) Inventors: Ryo Asai, Tokyo (JP); Tomoaki Kirino, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/754,997

(22) PCT Filed: Oct. 10, 2018

(86) PCT No.: PCT/JP2018/037649
§ 371 (c)(1),
(2) Date: Apr. 9, 2020

(87) PCT Pub. No.: WO2019/073987
PCT Pub. Date: Apr. 18, 2019

(65) Prior Publication Data
US 2020/0308126 A1 Oct. 1, 2020

(30) Foreign Application Priority Data
Oct. 11, 2017 (JP) .............................. JP2017-197724

(51) Int. Cl.
C07D 307/14 (2006.01)
(52) U.S. Cl.
CPC ................................. *C07D 307/14* (2013.01)
(58) Field of Classification Search
None
See application file for complete search history.

(56) References Cited

U.S. PATENT DOCUMENTS

| 2,857,397 A | 10/1958 | Cope |
| 2014/0135449 A1 | 5/2014 | Jeol |
| 2017/0217916 A1 | 8/2017 | Li et al. |
| 2020/0181105 A1* | 6/2020 | Asai ..................... C07D 307/52 |

FOREIGN PATENT DOCUMENTS

| CN | 107474026 A | 12/2017 | |
| CN | 108129426 * | 6/2018 | |
| JP | 2008-143832 A | 6/2008 | |
| JP | 2014-524953 A | 9/2014 | |
| JP | 2017-101179 A | 6/2017 | |
| JP | 2017-521430 A | 8/2017 | |
| WO | 2013/007585 A1 | 1/2013 | |
| WO | 2015/175528 A1 | 11/2015 | |
| WO | 2016/004867 A1 | 1/2016 | |
| WO | 2018/113599 A1 | 6/2018 | |
| WO | WO-2019073988 A1 * | 4/2019 | ............ C07B 61/00 |

OTHER PUBLICATIONS

Girka; Green Chem., 2017,19, 4074-4079. (Year: 2017).*
Pearlman; Organic Syntheses, Coll. vol. 5, p. 670 (1973). DOI:10.15227/orgsyn.049.0075 (Year: 1973).*
Stocker; Journal of Organic Chemistry 1962, 27, 2288-2289. (Year: 1962).*
Japan Patent Application Publication JP2008143832 (Jun. 26, 2008), Unverified Machine Translation from EPO. (Year: 2008).*
International Preliminary Report on Patentability and Written Opinion for PCT/JP2018/037649, dated Dec. 25, 2018, and English Translation submitted herewith (13 pages).
International Search Report for PCT/JP2018/037649, dated Dec. 25, 2018, and English Translation submitted herewith (5 pages).
Holm, David R. et al., "Kinetics of the Liquid Phase Hydrogenation of Furan Amines," Industrial & Engineering Chemistry Research, 1995, vol. 34, No. 10, pp. 3392-3398.
Komanoya, Tasuku et al., "Electronic Effect of Ruthenium Nanoparticles on Efficient Reductive Amination of Carbonyl Compounds," Journal of the American Chemical Society, 2017, vol. 139, No. 33, pp. 11493-11499.
Final Office Action issued in U.S. Appl. No. 16/755,277 dated Feb. 24, 2022 (13 pages).
VWR Analytical, Product Specification "Methanol," 2006 (1 page).

* cited by examiner

Primary Examiner — Daniel R Carcanague
(74) Attorney, Agent, or Firm — Fitch, Even, Tabin & Flannery LLP

(57) ABSTRACT

To provide a method that can efficiently produce 2,5-bis(aminomethyl)tetrahydrofuran. The method for producing 2,5-bis(aminomethyl)tetrahydrofuran, the method including subjecting 2,5-bis(aminomethyl)furan to a reaction with hydrogen source by using a hydrogenation catalyst to obtain 2,5-bis(aminomethyl)tetrahydrofuran.

13 Claims, No Drawings

METHOD FOR PRODUCING 2,5-BIS(AMINOMETHYL) TETRAHYDROFURAN

CROSS-REFERENCE TO RELATED APPLICATIONS

This application is a U.S. national phase application filed under 35 U.S.C. § 371 of International Application Number PCT/JP2018/037649, filed Oct. 10, 2018, designating the United States, which claims priority from Japanese Application Number 2017-197724, filed Oct. 11, 2017.

FIELD OF THE INVENTION

The present invention relates to a method for producing 2,5-bis(aminomethyl)tetrahydrofuran.

BACKGROUND OF THE INVENTION

Compounds having tetrahydrofuran structures are useful as raw materials or intermediates for products, such as resins, pharmaceuticals, and perfumes. Among them, 2,5-bis(aminomethyl)tetrahydrofuran includes amino groups as functional groups and thus is useful as epoxy resin curing agents or intermediate raw materials of compounds, and production methods for 2,5-bis(aminomethyl)tetrahydrofuran have been studied.

For example, as shown below, Patent Document 1 discloses that 2,5-bis(aminomethyl)tetrahydrofuran can be synthesized by using {5-(iminomethyl)furan-2-yl}methanamine or {5-(iminomethyl)furan-2-yl}methane azide as a starting material and performing a catalytic hydrogenation reaction in the presence of a Raney nickel catalyst.

[Chem.1]

CITATION LIST

Patent Literature

Patent Document 1: WO 2015/175528

SUMMARY OF INVENTION

In terms of ease of obtaining raw materials and keeping stable supply of 2,5-bis(aminomethyl)tetrahydrofuran, a method for efficiently producing 2,5-bis(aminomethyl)tetrahydrofuran from a raw material other than {5-(iminomethyl)furan-2-yl}methanamine or {5-(iminomethyl)furan-2-yl}methane azide in Patent Document 1 is demanded.

The present invention has been completed in view of the above situation, and an object of the present invention is to provide a production method that could efficiently produce 2,5-bis(aminomethyl)tetrahydrofuran.

As a result of diligent research on the method for producing 2,5-bis(aminomethyl)tetrahydrofuran, the present inventors have found that a hydrogenation reaction of 2,5-bis(aminomethyl)furan by using a catalyst enables efficient production of 2,5-bis(aminomethyl)tetrahydrofuran, and thereby completed the present invention.

That is, the present invention is as follows.

(1) A method for producing 2,5-bis(aminomethyl)tetrahydrofuran, the method including subjecting 2,5-bis(aminomethyl)furan to a reaction with a hydrogen source by using a hydrogenation catalyst to obtain 2,5-bis(aminomethyl)tetrahydrofuran.

(2) The production method according to (1), which is a one-pot synthesis.

(3) The production method according to (1) or (2), wherein the hydrogenation catalyst contains at least one selected from the group consisting of Fe, Co, Ni, Cu, Ru, Rh, Pd, Ir, Pt, Re, and Os.

(4) The production method according to (1) or (2), wherein the hydrogenation catalyst contains at least one selected from the group consisting of Fe, Co, Ni, Cu, Ru, Pd, Ir, Pt, Re, and Os.

(5) The production method according to (1) or (2), wherein the hydrogenation catalyst contains at least one selected from the group consisting of Fe, Co, Cu, Ru, Rh, Pd, Ir, Pt, Re, and Os.

(6) The production method according to (1) or (2), wherein the hydrogenation catalyst contains Rh.

(7) The production method according to any one of (1) to (6), wherein the hydrogen source contains at least one type of hydrogen and an alcohol having from 1 to 5 carbons.

(8) The production method according to any one of (1) to (7), wherein the reaction is performed at a hydrogen pressure of more than 0 MPa and 25 MPa or less.

(9) The production method according to any one of (1) to (8), wherein 2,5-bis(aminomethyl)furan is supplied to a reaction system.

The production method of the present invention is possible to efficiently provide 2,5-bis(aminomethyl)tetrahydrofuran and is an industrially advantageous production method. In addition, 2,5-bis(aminomethyl)tetrahydrofuran obtained by the production method of the present invention is useful as a raw material or an intermediate for products, such as resins, pharmaceuticals, and perfumes.

DESCRIPTION OF EMBODIMENTS

Embodiments of the present invention (hereinafter, referred to as "the present embodiment") are described in detail below; however, the present invention is not limited to these embodiments, and various modifications may be made without departing from the scope and spirit of the invention.

The contents of the present invention will be described in detail below. In the present specification, "from . . . to . . . " or "of . . . to . . . " is used to mean that the numerical values described before and after "to" are included as the lower limit value and the upper limit value, respectively.

The production method of the present embodiment is characterized by including subjecting 2,5-bis(aminomethyl)furan (hereinafter, also referred to as "H-BAF") to a reaction with a hydrogen source by using a hydrogenation catalyst to obtain 2,5-bis(aminomethyl)tetrahydrofuran (hereinafter, also referred to as "BAF"). Such a configuration allows efficient production of 2,5-bis(aminomethyl)tetrahydrofuran. Preferably, it can be obtained in a one-pot synthesis.

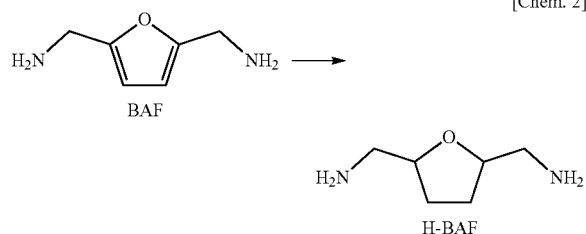

[Chem. 2]

As a result of research, by the inventors of the present invention, on the method for producing 2,5-bis(aminomethyl)tetrahydrofuran from 2,5-bis(aminomethyl)furan, the present inventors have found that 2,5-bis(aminomethyl)furan, which is a reaction substrate, is highly reactive and thus tends to generate a by-product. Specifically, formation of 2-(aminomethyl)-5-methyltetrahydrofuran below as a by-product was observed, In the following, Me is a methyl group.

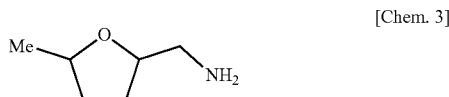

[Chem. 3]

Formation of a by-product leads to problems, such as reduced yield of the target product 2,5-bis(aminomethyl)tetrahydrofuran and necessity of purification to remove the by-product, thereby complicating the production process. In particular, because of the close similarity in structure to 2,5-bis(aminomethyl)tetrahydrofuran, which is the target product, 2-(aminomethyl)-5-methyltetrahydrofuran is a by-product difficult to separate from the target product by common purification methods.

As a result of further researches, by the inventors of the present invention, on the reaction conditions, the present inventors have found that a reaction of 2,5-bis(aminomethyl)furan with a hydrogen source by using a hydrogenation catalyst (in particular, a hydrogenation catalyst containing at least one selected form the group consisting of Fe, Co, Ni, Cu, Ru, Rh, Pd, Ir, Pt, Re, and Os) allows the olefin to selectively react and enables efficient production of 2,5-bis(aminomethyl)tetrahydrofuran without the formation of 2-(aminomethyl)-5-methyltetrahydrofuran.

2,5-Bis(aminomethyl)furan 2,5-Bis(aminomethyl)furan in the present embodiment is commercially available. In addition, 2,5-bis(aminomethyl)furan may be synthesized from a well-known compound, such as 5-hydroxymethyl furfural or 5-(chloromethyl)furfural, using an organic synthesis technique.

Hydrogenation Catalyst

The hydrogenation catalyst in the present embodiment preferably includes at least one metal selected from the group consisting of Fe, Co, Ni, Cu, Ru, Rh, Pd, Ir, Pt, Re, and Os. Of these metals, one may be used alone, or two or more may be used in combination.

As described above, 2,5-bis(aminomethyl)tetrahydrofuran is highly reactive and thus tends to generate a by-product. Especially, it is believed that, for the at least one metal selected from the group consisting of Fe, Co, Ni, Cu, Ru, Rh, Pd, Ir, Pt, Re, and Os, its activity as a catalyst is not too high, thereby suppressing the formation of 2-(aminomethyl)-5-methyltetrahydrofuran, which is the by-product.

The metal described above may be supported on a carrier. The carrier is not particularly limited, as long as it is a carrier commonly used as a catalyst carrier, and its examples include inorganic oxides, activated carbon, and ion exchange resins. Specific examples of the inorganic oxides include silica ($SiO_2$), titania ($TiO_2$), zirconia ($ZrO_2$), alumina ($Al_2O_3$), magnesium oxide (MgO), and complexes of two or more of these inorganic oxides (for example, such as zeolite).

For the hydrogenation catalyst, in a preferred embodiment, the hydrogenation catalyst includes at least one selected from the group consisting of Fe, Co, Cu, Ru, Rh, Pd, Ir, Pt, Re, and Os.

In another preferred embodiment, the hydrogenation catalyst includes at least one selected from the group consisting of Fe, Co, Cu, Ru, Pd, Ir, Pt, Re, and Os.

In still another preferred embodiment, the hydrogenation catalyst includes at least one of Ru and Rh.

In still another preferred embodiment, the hydrogenation catalyst includes Rh.

Specific examples of the hydrogenation catalyst include iron (Fe) catalysts, such as reduced iron; cobalt (Co) catalysts, such as reduced cobalt and Raney cobalt; nickel (Ni) catalysts, such as reduced nickel, nickel oxide, and Raney nickel (hereinafter, also referred to as "Raney-Ni"); copper (Cu) catalysts, such as copper (II) chloride, copper (I) chloride, copper (0), copper (I) oxide, and copper (II) oxide; ruthenium (Ru) catalysts, such as ruthenium/carbon and ruthenium/alumina; rhodium (Rh) catalysts, such as rhodium/carbon and rhodium/alumina; rhenium (Re) catalysts, such as platinum-supported perrhenic acid; and osmium (Os) catalysts, such as osmium/carbon.

An amount of the catalyst relative to the amount of 2,5-bis(aminomethyl)furan may be appropriately adjusted, and typically it is from 1 to 200 parts by mass relative to the mass of 2,5-bis(aminomethyl)furan. The amount of the catalyst is preferably from 1 to 150 parts by mass and more preferably from 1 to 100 parts by mass relative to the mass of 2,5-bis(aminomethyl)furan.

Hydrogen Source

The hydrogen source in the present embodiment is not particularly limited, as long as it is a hydrogen source that can reduce olefins, and its examples suitably include hydrogen and alcohols having from 1 to 5 carbons. One of these hydrogen sources may be used alone, or two or more of them may be used in combination.

Specific examples of the alcohols having from 1 to 5 carbons include methanol, ethanol, n-propanol, isopropanol, n-butanol, sec-butanol, isobutanol, tert-butanol, n-amyl alcohol, sec-amyl alcohol, 3-pentanol, 2-methyl-1-butanol, 3-methyl-1-butanol, 2-methyl-2-butanol, 3-methyl-2-butanol, and neopentyl alcohol. One of these alcohols having from 1 to 5 carbons may be used alone, or two or more of them may be used in combination.

Among these, preferred alcohols having from 1 to 5 carbons are methanol, ethanol, n-propanol, isopropanol, n-butanol, sec-butanol, n-amyl alcohol, and sec-amyl alcohol.

The reaction of the present embodiment may be performed in the presence of a solvent. The solvent is not particularly limited, and it is selected appropriately according to things such as the reaction temperature and the reaction product.

The solvent is not particularly limited, as long as the solvent is possible to dissolve a portion or a whole amount of 2,5-bis(aminomethyl)furan and does not interfere with the hydrogenation reaction, and its examples include aromatic hydrocarbon solvents, amide solvents, ether solvents, alcohol solvents, and halogen solvents. Ether solvents are preferred. One of these solvents may be used alone, or two or more of them may be used in combination.

Specific examples of the aromatic hydrocarbon solvents include benzene and toluene.

Specific examples of the amide solvents include acetonitrile, N,N-dimethylacetamide, and N,N-dimethylformamide. It is preferable that the solvent used in the present invention is substantially free of xylene. Substantially free means that, xylene is in an amount of 10 mass % or less of the solvent, preferably 5 mass % or less, more preferably 3 mass % or less, even more preferably 1 mass % or less, and still more preferably 0 mass %.

Specific examples of the ether solvents include tetrahydrofuran (hereinafter, also referred to as "THF") and diethyl ether.

Specific examples of the alcohol solvents include methanol, ethanol, and isopropanol. The alcohol solvents can serve as the hydrogen source.

Specific examples of the halogen solvents include dichloromethane, dichloroethane, and chloroform.

Whether or not the solvent is used, or its amount to be used is not particularly limited, but in terms of productivity and energy efficiency, the solvent is used in an amount of preferably from 0.5 to 100 times by mass, more preferably from 1.0 to 50 times by mass, and even more preferably from 1.0 to 20 times by mass, relative to the mass of 2,5-bis(aminomethyl)furan.

The solvent in the present embodiment preferably has a low water content. The water content in the solvent is preferably from 0 to 3.0 mass %, more preferably from 0 to 2.0 mass %, and even more preferably from 0 to 1.0 mass %. The solvent having a low water content can suppress the formation of a by-product and also improve the selectivity in the formation of the target product 2,5-bis(aminomethyl)tetrahydrofuran.

In the present embodiment, an aspect, in which 95 mass % or more of the solvent is an ether solvent is exemplified.

Reaction Conditions

Specific examples of the production method of the present embodiment include a method of mixing 2,5-bis(aminomethyl)furan, a hydrogenation catalyst, and a hydrogen source, as well as a solvent if necessary; and subjecting them to a reaction. In the present invention, typically 2,5-bis(aminomethyl)furan is supplied to the reaction system. Charging of the raw material 2,5-bis(aminomethyl)furan directly into the reaction system (for example, reactor, reaction pot) as described above allows efficient production of 2,5-bis(aminomethyl)tetrahydrofuran.

2,5-bis(aminomethyl)furan, the hydrogenation catalyst, the solvent, and the hydrogen source may be mixed in any order. In terms of operational efficiency, in the production method of the present embodiment, preferably 2,5-bis(aminomethyl)furan and the hydrogenation catalyst are mixed in advance, and then the hydrogen source is added.

In the production method of the present embodiment, to prevent ignition, the hydrogenation catalyst may be added in an inert atmosphere with gases like nitrogen or argon, depending on the hydrogenation catalyst; or the hydrogenation catalyst may be suspended in a solvent and added as a suspension.

In the production method of the present embodiment, when hydrogen is used as the hydrogen source, the reaction is preferably performed at a hydrogen pressure of more than 0 MPa and 25 MPa or less. The hydrogen pressure is more preferably 0.5 MPa or more and 15 MPa or less, and even more preferably 1.0 MPa or more and 10 MPa or less.

The reaction temperature is adjusted appropriately, such as the type of the solvent, and is typically from 40 to 200° C., preferably from 50 to 120° C., more preferably from 50 to 110° C., and even more preferably from 70 to 115° C.

The reaction time is appropriately adjusted by monitoring the progress of the reaction using a method such as GC-MS and is typically from 1 minute to 24 hours, preferably from 0.5 to 3 hours, and more preferably from 0.5 to 2 hours.

The reaction mixture and the catalyst after the reaction can be separated by a typical method, such as precipitation, centrifugation, or filtration. The catalyst is preferably separated in an inert gas atmosphere, such as nitrogen or argon, as appropriate according to the catalyst used to prevent ignition.

In addition, the resulting reaction solution may be concentrated as necessary, and then the residue may be used as a raw material or an intermediate, or the reaction mixture may be appropriately post-treated and purified. Specific examples of the method for the post-treatment include well-known purification methods, such as extraction, distillation, and chromatography. Two or more of these purification methods may be performed in combination.

EXAMPLES

Hereinafter, the present invention will be described in further detail with reference to the experimental examples, though the present invention is not limited to the following experimental examples.

Example 1

Into a pressure-resistant autoclave, 0.5 g of 2,5-bis(aminomethyl)furan, 3 mL of THF as a solvent, and 0.1 g of Ru/alumina ($Al_2O_3$) as a catalyst (the amount of Ru catalyst is 5 mass %, and hereinafter it may be indicated as "5 mass % Ru/alumina".) were charged, and then the hydrogen pressure was increased to 3 MPaG. Ru/alumina, which was reduced beforehand at 150° C. for 12 hours, was used.

The reaction was then performed while the temperature was maintained at 90° C. for 1 hour, and terminated by cooling the pressure-resistant autoclave with ice water.

The catalyst was removed by filtering the catalyst and the reaction liquid in an argon gas stream, and the filtrate containing the product was subjected to an accurate mass measurement by CI method. The accurate mass measurement by CI method was performed using a GC-MS spectrometer, Agilent 7890B GC/5977 MSD (available from Agilent Technologies, Inc.).

In addition, a portion of the residue obtained by concentrating the filtrate was dissolved in deuterated chloroform, and $^1$H-NMR and $^{13}$C-NMR measurements were performed. An NMR measuring device, JNM-ECA500 (500 MHz) available from JEOL Ltd., was used.

2,5-bis(aminomethyl)furan available from Toronto Research Chemicals was used.

THF, available from Wako Pure Chemical Industries, Ltd. for spectroscopic analysis, was used.

Ru/alumina, which is a ruthenium catalyst supported on alumina, available from N.E. Chemcat Corporation was used.

Yield of Product

The proportion of the area value of 2,5-bis(aminomethyl)tetrahydrofuran to the area value of all peaks in GC-FID detection intensities (area values) determined the yield of 2,5-bis(aminomethyl)tetrahydrofuran.

Specifically, the area value was determined from GC-FID detection intensities (area values) obtained by GC-FID measurement of the reaction liquid, and the proportion of the area value of 2,5-bis(aminomethyl)tetrahydrofuran to the area values of all the peaks was determined to be 82%. And thus, the yield of 2,5-bis(aminomethyl)tetrahydrofuran was 82%.

Identification of Product (Results of $^1$H-NMR, $^{13}$C-NMR, and Accurate Mass Measurement by CI Method)

$^1$H-NMR and $^{13}$C-NMR measurements of the product obtained in Example 1 were performed, and the chemical shifts from 2,5-bis(aminomethyl)furan, which is the raw material, were subtracted. The chemical shifts then revealed that the resulting compound had: a tetrahydrofuran ring based on the $^1$H-NMR measurement and a symmetric molecular structure based on the $^{13}$C-NMR measurement. Further, the $^1$H-NMR and $^{13}$C-NMR shifts of 2,5-bis(aminomethyl)tetrahydrofuran calculated by ChemDraw essentially matched the measured chemical shifts.

Furthermore, an accurate molecular weight of the resulting product determined by CI method was 131, which corresponded to a molecular weight of the molecule in which a proton coordinated as a counter cation to 2,5-bis(aminomethyl)tetrahydrofuran, and thus the product was identified as the target product. No formation of 2-(aminomethyl)-5-methyltetrahydrofuran was observed.

Example 2

Example 2 was performed in the same manner as in Example 1 except that 5 mass % Pd/carbon (C) was used as the catalyst.

The yield of 2,5-bis(aminomethyl)tetrahydrofuran was 41% as determined in the same manner as in Example 1. Identification of the product performed in the same manner confirmed the formation of 2-(aminomethyl)-5-methyltetrahydrofuran together with 2,5-bis(aminomethyl)tetrahydrofuran.

Pd/carbon (C), a Pd catalyst supported on carbon, available from N.E. Chemcat Corporation was used.

Example 3

Into a pressure-resistant autoclave, 20 g of 2,5-bis(aminomethyl)furan, 8 g of 5 mass % Ru/alumina as a catalyst, and 120 mL of THF as a solvent were charged, and then the hydrogen pressure was increased to 6 MPaG. The reaction was performed while the temperature was maintained at 90° C. for 1 hour and terminated by cooling the pressure-resistant autoclave with ice water. The catalyst was removed by filtering the catalyst and the reaction liquid in an argon gas stream, the filtrate containing the product was obtained and then concentrated. In the present example, Ru/alumina, which was reduced beforehand at 150° C. for 12 hours, was used.

Analysis of the resulting product with a GC-MS spectrometer Agilent 7890B GC/5977 MSD (available from Agilent Technologies, Inc.) indicated that the amount of 2,5-bis(aminomethyl)tetrahydrofuran was 91 mol %, the amount of 2,5-bis(aminomethyl)furan was 0 mol %, and the amount of 2-(aminomethyl)-5-methyltetrahydrofuran was 9 mol %.

2,5-Bis(aminomethyl)furan available from Toronto Research Chemicals was used.

Ru/alumina, a ruthenium catalyst supported on alumina, available from N.E. Chemcat Corporation was used.

Example 4

Into a pressure-resistant autoclave, 20 g of 2,5-bis(aminomethyl)furan, 8 g of 5 mass% Rh/C as a catalyst, and 120 mL of THF as a solvent were charged, and then the hydrogen pressure was increased to 6 MPaG. The reaction was performed while the temperature was maintained at 90° C. for 1 hour and then terminated by cooling the pressure-resistant autoclave with ice water. The catalyst was removed by filtering the catalyst and the reaction liquid in an argon gas stream. After the filtrate containing the product was obtained, it was concentrated and purified by distillation under reduced pressure at a temperature of 120° C. and at 1 mbar. Analysis of the resulting product with a GC-MS spectrometer Agilent 7890B GC/5977 MSD (available from Agilent Technologies, Inc.) indicated that the amount of 2,5-bis(aminomethyl)tetrahydrofuran was 100 mol% .

2,5-Bis(aminomethyl)furan available from Toronto Research Chemicals was used.

Rh/C, available from N.E. Chemcat Corporation was used.

The invention claimed is:

1. A method for producing 2,5-bis(aminomethyl)tetrahydrofuran, the method comprising supplying 2,5-bis(aminomethyl)furan to a reaction system and subjecting the 2,5-bis(aminomethyl)furan to a reaction with a hydrogen source by using a hydrogenation catalyst to obtain 2,5-bis(aminomethyl)tetrahydrofuran,
    wherein the hydrogenation catalyst comprises at least one selected from the group consisting of Fe, Cu, Ru and Rh.

2. The production method according to claim 1, which is a one-pot synthesis.

3. The production method according to claim 1, wherein the hydrogenation catalyst comprises Ru.

4. The production method according to claim 1, wherein the hydrogenation catalyst comprises Rh.

5. The production method according to claim 1, wherein the hydrogen source comprises at least one of hydrogen or an alcohol having from 1 to 5 carbons.

6. The production method according to claim 1, wherein the reaction is performed at a hydrogen pressure of more than 0 MPa and 25 MPa or less.

7. The production method according to claim 2, wherein the hydrogenation catalyst comprises Rh.

8. The production method according to claim 2, wherein the hydrogen source comprises at least one of hydrogen and an alcohol having from 1 to 5 carbons.

9. The production method according to claim 2, wherein the reaction is performed at a hydrogen pressure of more than 0 MPa and 25 MPa or less.

10. The production method according to claim 4, wherein the reaction is performed at a hydrogen pressure of more than 0 MPa and 25 MPa or less.

11. The production method according to claim 5, wherein the reaction is performed at a hydrogen pressure of more than 0 MPa and 25 MPa or less.

12. The production method according to claim 1,
    wherein the reaction is performed in presence of a solvent; and
    an amount of the solvent is from 1.0 to 20 times by mass, relative to the mass of 2,5-bis(aminomethyl)furan.

13. The production method according to claim 12, wherein the solvent includes an ether solvent.

\* \* \* \* \*